United States Patent [19]

Huene et al.

[11] Patent Number: 5,376,121
[45] Date of Patent: Dec. 27, 1994

[54] DUAL CONSTRAINT ELBOW PROSTHESIS

[75] Inventors: Donald R. Huene, Fresno; Erik Rinde, Ventura, both of Calif.

[73] Assignee: Techmedica, Inc., Camarillo, Calif.

[21] Appl. No.: 19,186

[22] Filed: Feb. 17, 1993

Related U.S. Application Data

[63] Continuation-in-part of Ser. No. 6,126, Jan. 19, 1993, Pat. No. 5,314,484, which is a continuation of Ser. No. 740,918, Aug. 6, 1991, abandoned.

[51] Int. Cl.⁵ .................................................. A61F 2/38
[52] U.S. Cl. .......................................................... 623/20
[58] Field of Search ........................................ 623/18.21

[56] References Cited

U.S. PATENT DOCUMENTS

| 3,638,243 | 2/1972 | Campbell, Jr. et al. | 3/1 |
|---|---|---|---|
| 3,708,805 | 1/1973 | Scales et al. | 3/1 |
| 3,765,033 | 10/1973 | Goldberg et al. | 3/1 |
| 3,772,709 | 11/1973 | Swanson | 3/1 |
| 3,816,854 | 6/1974 | Schlein | 3/1 |
| 3,824,630 | 7/1974 | Johnson | 3/1 |
| 3,852,831 | 12/1974 | Dee | 3/1 |
| 3,863,274 | 2/1975 | Glabiszewski | 3/27 |
| 3,868,730 | 3/1975 | Kaufer et al. | 3/1 |
| 3,909,854 | 10/1975 | Martinez | 3/1.911 |
| 3,990,117 | 11/1976 | Pritchard et al. | 3/1.91 |
| 4,038,704 | 8/1977 | Ring | 3/1.91 |
| 4,057,858 | 11/1977 | Helfet | 3/1.91 |
| 4,079,469 | 3/1978 | Wadsworth | 3/1.91 |
| 4,088,130 | 5/1978 | Applegate | 128/80 F |
| 4,129,902 | 12/1978 | Harmon | 3/1.91 |
| 4,131,956 | 1/1979 | Treace | 3/1.91 |
| 4,224,695 | 9/1980 | Grundei et al. | 3/1.91 |
| 4,280,231 | 7/1981 | Swanson | 3/1.91 |
| 4,293,963 | 10/1981 | Gold et al. | 3/1.91 |
| 4,378,607 | 4/1983 | Wadsworth | 3/1.91 |
| 4,383,337 | 5/1983 | Volz et al. | 3/1.91 |
| 4,520,802 | 6/1985 | Mercer et al. | 128/80 C |
| 4,538,306 | 9/1985 | Dörre et al | 623/20 |
| 4,777,941 | 10/1988 | Borig et al. | 128/80 |
| 4,802,467 | 2/1989 | Pansiera | 128/88 |
| 4,881,299 | 11/1989 | Young et al. | 16/371 |
| 4,915,098 | 4/1990 | Young et al. | 128/88 |
| 5,000,170 | 3/1991 | Young et al. | 128/80 C |

FOREIGN PATENT DOCUMENTS 2177603 1/1987 United Kingdom .
2182714 5/1987 United Kingdom .

OTHER PUBLICATIONS

De Puy, Total Elbow System, 1988.
Pritchard, Mark II Total Elbow, 1983.
Pritchard, Pritchard ERS with Ponocoat, 1987.

Primary Examiner—Randy C. Shay
Attorney, Agent, or Firm—Joseph W. Berenato, III

[57] ABSTRACT

An artificial elbow has a humeral member and an ulnar member. A connecting segment has first and second ends. A first pin assembly connects the humeral member to the first end for pivotal rotation relative thereto in response to a first torque. A second pin assembly connects the ulnar member to the second end for pivotal rotation relative thereto in response to a second torque. The second torque is less than the first torque.

32 Claims, 2 Drawing Sheets

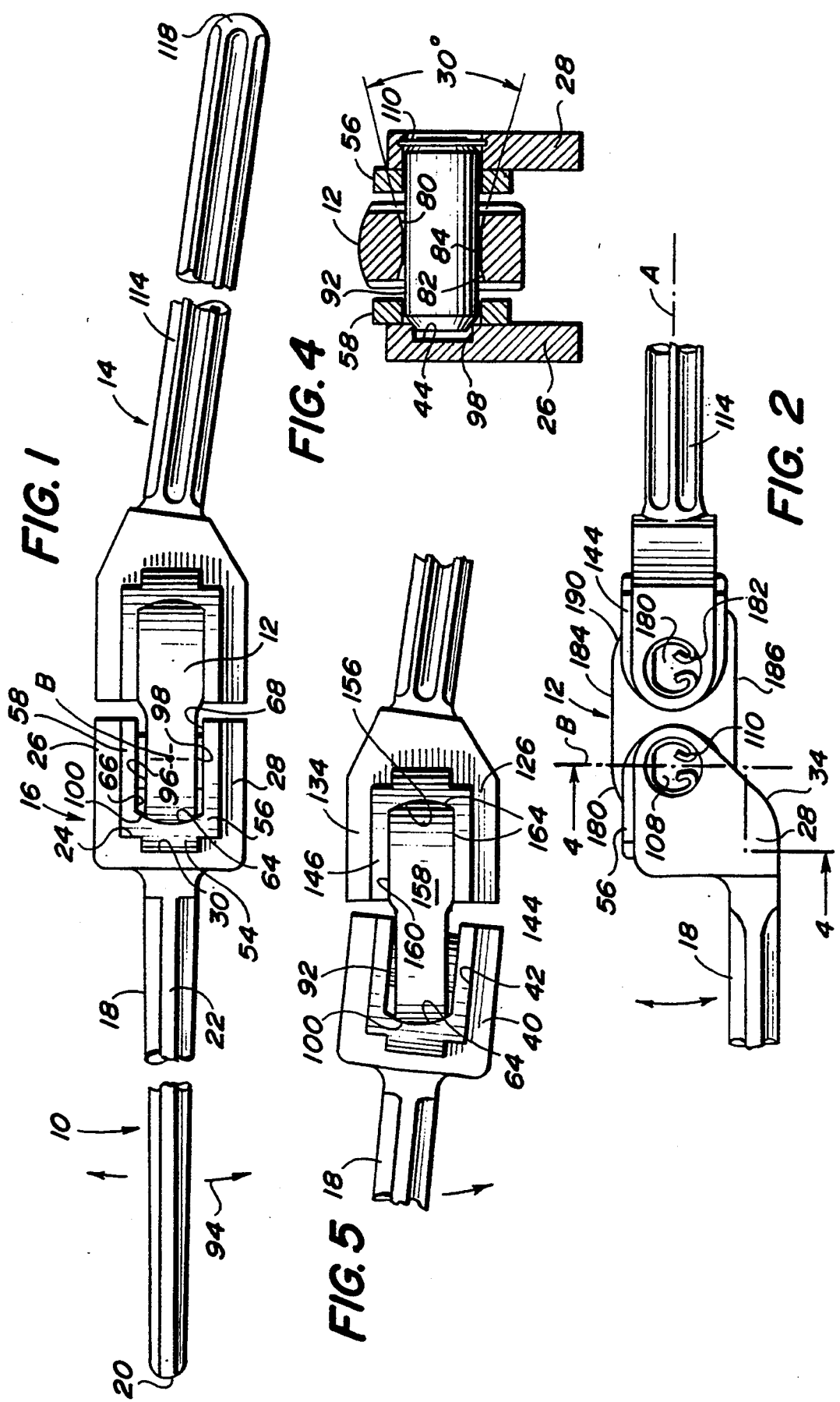

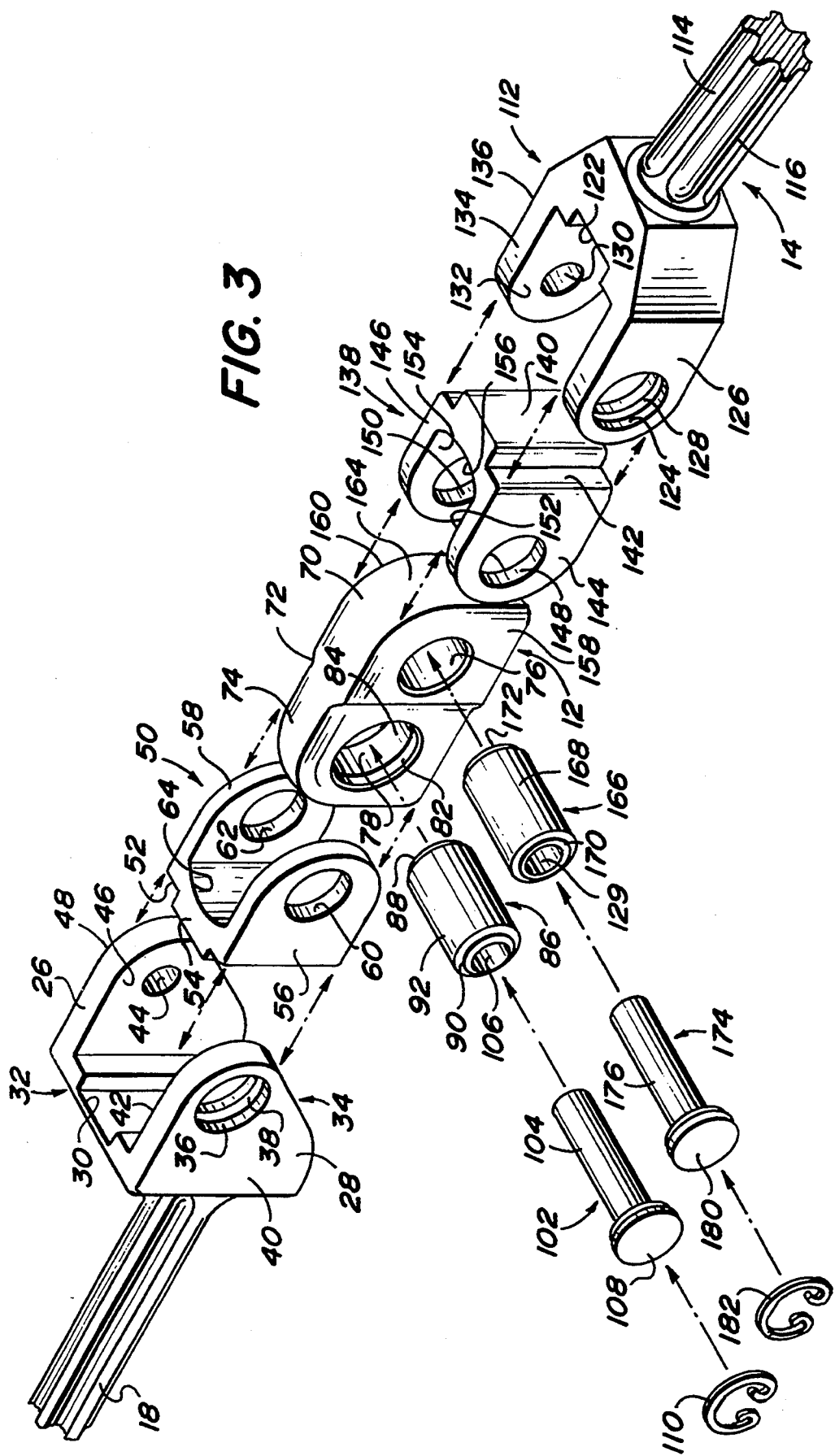

DUAL CONSTRAINT ELBOW PROSTHESIS

CROSS-REFERENCE TO RELATED APPLICATIONS

This application is a continuation-in-part of application Ser. No. 08/006,126, filed Jan. 19, 1993 now U.S. Pat. No. 5,314,484, which is a continuation of application Ser. No. 740,918, filed Aug. 6, 1991, now abandoned.

FIELD OF THE INVENTION

The invention is a dual constraint elbow prosthesis which is implantable into the ulnar and humeral bones of a patient. The ulnar member is freely rotatable about a pivot pin carried by a connecting segment. The connecting segment is rotatable relative to the humeral bone only in response to a predetermined torque.

BACKGROUND OF THE INVENTION

A human elbow permits pivoting movement of an ulnar bone relative to the connected humeral bone. Should the elbow joint become damaged by disease, accident, or the like, then the ulnar and humeral bones may not have an acceptable level of relative pivotal motion. Although artificial elbows have been proposed, none achieves the range of mobility which approaches that which is naturally occurring.

For replacement of an elbow to occur, then there is a need to provide a connection to the ulnar bone and the humeral bone. One means for connecting the bones is by implanting into each an artificial member which extends into the shaft or medullary canal thereof. These members may be cemented within the canal, with their adjacent free ends interconnected by some sort of hinge mechanism. A particular disadvantage of a single hinge artificial elbow is due to the transfer of force from the hinge into the bone cement interface of the humeral or ulnar member. Eventually the humeral or ulnar member may become loosened within its medullary canal by this unrestricted or unmitigated force transfer. The longevity of single hinge implants subjected to these high stresses has been unsatisfactory, and replacement may be required.

Prior application Ser. No. 07/740,918, the disclosure of which is incorporated herein by reference, is directed to an implantable artificial elbow wherein two hinge points are provided by a connecting link which is pivotally connected to the free ends of the ulnar and humeral members. The double hinge connection minimizes the transfer of force into both medullary canals of the humeral and ulnar bones, with the result that implantation longevity is greatly increased. Furthermore, because of the double hinge mechanism, which to a certain extent resembles a double hinge nut cracker, the ulnar and humeral bones can be pivoted to a greater extent relative to each other. The connecting link provides a reservoir or space within which the muscle mass is positioned.

In addition to pivotal motion of the ulnar relative to the humeral bone, the human elbow permits the ulnar to move sideways transverse to its pivot axis. No artificial elbow known to us has this capability.

Another disadvantage of prior artificial elbows is the use of metal components, which wear on account of the single pivoting motion. Should the components become worn, then the patient will eventually lose motion with the prosthesis and may require a replacement. Because the components have worn, then the load bearing surfaces must be replaced in their entirety by another surgical procedure.

The disclosed invention is an artificial elbow which has a dual hinge pivoting mechanism, and the ulnar member is maintained in a semi-constrained state while the humeral member is maintained more rigidly restricted and constrained so that a more natural motion may occur without instability. Furthermore, sideways motion of the ulnar is permitted because of the manner in which the ulnar member is attached to the connecting segment. In addition, polymeric materials are provided at contact points, in order to minimize wear of metal components. The polymeric components are easily replaced so that the ulnar and humeral members may be left in place when worn components are replaced. The differential torque requirements of the two pivots restricts the simultaneous joint pivot motion that could result in joint instability.

OBJECTS AND SUMMARY OF THE INVENTION

The primary object of the disclosed invention is a dual hinge artificial elbow in which the ulnar member is maintained semi-constrained, while the humeral member is maintained constrained so that the ulnar member moves preferentially to the humeral member.

An artificial elbow comprises a humeral member and an ulnar member. A connecting segment has first and second ends. First means connect the humeral member to the first end of the connecting segment for pivotal rotation relative thereto in response to a first torque, and second means connect the ulnar member to the second end of the connecting segment for pivotal motion relative thereto in response to a second torque. The second torque requirement is much less than the first torque.

An artificial elbow comprises a humeral member having a first yoke at an end thereof. An ulnar member has a second yoke at an end thereof. A connecting segment has integral first and second portions, with the first portion having a thickness exceeding the thickness of the second portion. The first yoke is frictionally secured to the first portion and is pivotal relative thereto, and the second yoke is relatively loosely secured to the second portion and is pivotal relative thereto.

These and other objects and advantages of the invention will be readily apparent in view of the following description and drawings of the above described invention.

DESCRIPTION OF THE DRAWINGS

The above and other objects and advantages and novel features of the present invention will become apparent in the following detailed description of the preferred embodiment of the invention illustrated in the accompanying drawings, wherein:

FIG. 1 is a fragmentary top plan view of the artificial elbow of the invention, with the double arrow indicating pivotal sideways motion;

FIG. 2 is a fragmentary elevational view thereof;

FIG. 3 is a fragmentary exploded assembly drawing of the invention;

FIG. 4 is a cross-sectional view, taken along the line 4—4 of FIG. 2, and viewed in the direction of the arrows and with the double arrow indicating pivotal vertical motion; and FIG. 5 is a fragmentary plan view with the ulnar member in a sideways pivoted position.

DESCRIPTION OF THE INVENTION

Artificial elbow prosthesis E, as best shown in FIGS. 1 and 3, includes an ulnar member 10, connecting segment 12, and humeral member 14. The ulnar and humeral members 10 and 14, respectively, are each sized to be received within a respective medullary canal of the recipient. The ulnar and humeral members 10 and 14 are, preferably, made from a surgical titanium alloy, such as Ti-6A1-4V ELI.

Ulnar member 10 has a U-shaped yoke 16 from which spike 18 extends. Spike 18 tapers from yoke 16 to its rounded terminal end 20, thereby having a greater diameter at yoke 16 than at end 20 in order to be received in the medullary canal of the ulnar bone. Spike 18 has a series of scalloped ribs 22 extending the length thereof, in order to receive cement or other bone adhesive for securing the ulnar member 10 within the ulnar bone.

Yoke 16 has a base 24 from which arms 26 and 28 extend in parallel from lateral edges thereof. Base 24 has a groove 30 extending the length thereof generally transverse to the direction in which spike 18 extends. Base 24 and its integral arms 26 and 28 have an upper generally planar portion 32, and a lower arcuate portion 34 from which integral spike 18 extends. Arm 28 has an aperture 36 therethrough, with a groove 38 formed therein intermediate spaced sides 40 and 42. Arm 26, on the other hand, has a detent 44 formed on inside surface 46 thereof, so that the exterior side surface 48 presents a smooth and uninterrupted surface. Detent 44 is coaxial with aperture 36, and has a diameter less than the diameter of aperture 36.

Saddle bearing 50 is U-shaped and complements yoke 16. Saddle bearing 50 has a base 52 from which tongue 54 extends the length thereof. Tongue 54 and base 52 have dimensions complementing the dimensions of base 24 and groove 30, so that the tongue 54 may slide within groove 30 in the event the saddle bearing 50 subsequently needs to be changed or replaced. Because saddle bearing 50 is slidable relative to yoke 16, then ulnar member 10 may remain fixed within its ulnar bone while the saddle bearing is being replaced.

Saddle bearing 50 has arms 56 and 58 which extend in spaced parallel relation from lateral edges of base 52. Each of arms 56 and 58 is juxtaposed to and in contact with an adjacent one of arms 28 and 26, respectively. Arms 56 and 58 have apertures 60 and 62, respectively therethrough, with the apertures 60 and 62 being coaxial and coaxial with the aperture 36 and generally of the same diameter thereof. Base 52 has an arcuate contact portion 64 on the interior thereof.

The saddle bearing 50 is, preferably, comprised of an ultra high molecular weight polyethylene ("UHMWPE") which is a polymeric material resistant to abrasion and attack by body fluids. Arm 58 has an inner side surface 66 which is spaced from inner side surface 68 of arm 56. Each of side surfaces 66 and 68 extends in parallel from lateral ends of contact portion 64.

Connecting link 12, as best shown in FIGS. 1 and 3, has a first relatively thick portion 70, tapered intermediate portion 72, and second relatively thin portion 74. Connecting segment 12 is formed from an ultra high molecular weight polyethylene material, preferably the same material as the saddle bearing 50. Link portions 70 and 74 have apertures 76 and 78 extending therethrough in spaced parallel relation. The axes or apertures 76 and 78 define a first plane A, with the spike 18 extending parallel to and spaced from plane A, as best shown in FIG. 2. Aperture 78 is sized to be no less than the diameter of aperture 36.

Aperture 78 is coaxial with aperture 36 when the connecting link 12 is received within the interior space of saddle bearing 50, and when the saddle bearing 50 is received within the interior space of yoke 16. Aperture 78 has chamfers 80 and 82, as best shown in FIG. 4, extending inwardly from the faces thereof toward each other. The chamfers 80 and 82 subtend an angle of 30° as best shown in FIG. 4. The chamfers 80 and 82 do not extend to each other, and a cylindrical base portion 84 extends therebetween.

UHMWPE cylindrical bearing 86 has a tapered end 88 at one end, and a correspondingly tapered end 90 at the opposite end. Tapered end 88, as best shown in FIG. 4, is received within detent 44 in arm 26 of yoke 16, with the cylindrical wall 92 thereof sized to fit aperture 62 of arm 58. Tapered end 90, on the other hand, is received within aperture 36 of arm 28, and terminates therein to permit external access to groove 38. The cylindrical wall 92 corresponds to the diameter of the aperture 60 of arm 56 of saddle bearing 50, and is slightly spaced from base portion 84 of connecting segment second portion 74. Because of the slight gap between wall 92 and base portion 84, as well as chamfers 80 and 82, a slight sideways rocking action, as illustrated by the double arrow 94 of FIG. 1, may be achieved by ulnar member 10.

Second portion 74 has side surfaces 96 and 98 which, as best illustrated in FIG. 1, are spaced from the adjacent surfaces 66 and 68 of arms 58 and 56, respectively. Second portion 74 has arcuate end 100 which has a curvature corresponding to the curvature of contact portion 64, so that side ways pivoting of ulnar member 10 is delimited by engagement of end portion 100 with contact portion 64 and by engagement with the adjacent walls 66 and 68.

Metal pin 102, formed from the same material as ulnar member 10, has a barrel 104 extending through aperture 106 of bearing 86. Head 108 is integral with barrel 104. Snap ring 110, also formed from the same metal alloy, is received within groove 38 in arm 28, thereby securing pin 102 within yoke 16. Because of the gap between wall 92 and base 84, then the ulnar member 10 is unconstrained relative to connecting segment 12, and may pivot about bearing 86 with essentially no resistance being presented.

Humeral member 14 has a yoke 112 integral with spike 114. Humeral member 14 is formed from the same alloy as is the ulnar member 10. Spike 114 has a plurality of ribs 116 which extend from yoke 112 to rounded end 118 for receiving the bone cement or adhesive. Unlike ulnar member 10, however, the spike 114 of humeral member 14 is essentially a constant cross-sectional dimension between yoke 112 and end 118. Furthermore, as best illustrated in FIG. 1, spike 114 extends angularly from yoke 112 in order to conform to the carrying angle of a human arm. Also, as best illustrated in FIG. 2, spike 114 extends along plane A, and in spaced parallel relation to spike 18.

Yoke 112 has a base 120 with a groove 122. Aperture 124 is formed in arm 126 thereof, with groove 128 formed within aperture 124. Detent 130, on the other hand, is formed within side surface 132 of arm 134, so that the exterior surface 136 is smooth and uninterrupted. Arms 126 and 134 extend in spaced parallel relation from lateral edges of base 120.

Saddle bearing 138 is formed from UHMWPE, and has a tongue 140 extending from base 142. Tongue 140 and base 142 are dimensioned to complement the groove 122 and base 120 of yoke 112, and tongue 140 is slidable relative to groove 122. Saddle bearing 138 has spaced parallel arms 144 and 146 with coaxial apertures 148 and 150, respectively, therethrough. The arms 144 and 146 rest against the corresponding surfaces of the arms 126 and 134, while the tongue 140 and groove 122 prevent rotation thereof. Inner surfaces 152 and 154 extend from arcuate contact portion 156 of base 142.

First portion 70 of connecting segment 12 has surfaces 158 and 160 which rest against the surfaces 152 and 154 of saddle bearing 138. Arcuate end portion 164 complements contact portion 156 but, because the first portion 70 is at least as thick as the interior space between the surfaces 152 and 154, no pivoting of end portion 164 about contact portion 156 may occur. We prefer that the portion 70 be frictionally engaged with the walls 152 and 154, in order to constrain the humeral member relative to segment 12.

Cylindrical bearing 166, which is similar to the bearing 86, has a cylindrical wall 168 with chamfered ends 170 and 172. As with the bearing 86, chamfered end 172 is received within detent 130, with the end 170 being inwardly spaced relative to groove 128.

Metal pin 174 has a barrel 176 extending through aperture 178 in bearing 166. Head 180 is integral with barrel 176, and pin 174 is secured in position by a snap ring 182 received within groove 128.

As best illustrated in FIG. 2, ulnar member 10 may pivot about axis B extending transverse to pin 102, in a side wise relation relative to connecting segment 12, because surfaces 96 and 98 are axially spaced from the corresponding surfaces 66 and 68 of saddle bearing 50. The spacing between the surfaces of the connecting segment 12 and the corresponding surfaces of the saddle bearing 50 and the chamfered ends 80 and 82 permit a rotation of about 8° to about 10° of side ways or varus valgus motion. The apertures 76, 148 and 150 are bored without a chamfer, so that the connecting segment 12 does not permit sideways pivoting. Thus the ulnar member may pivot about on axis, 3 extending transverse to the pin 102.

Connecting segment has top surface 184 and bottom surface 186, which extend in planar parallel relations. As best shown in FIG. 2, top surface 184 has rounded ends 188 and 190 which merge into contact portions 100 and 164, respectively. Because of the arguate natures of ends 188 and 190, ulnar member 10 will pivot 90° about pin 102 until contact portion 64 engages surface 184. Surface 184 therefore provides a stop which prevents further rotation of ulnar member 10 about pin 102. Should more than 90° movement of the ulnar bone be needed, then connecting segment 12 then begins to pivot about pin 174. Pivoting occurs until surface 184 engages contact portion 156, which thereby provides a stop to further pivoting motion. Segment 12 may pivot about pin 174 no more than 90°, so that the total combined pivot is 180°.

It can be seen in FIG. 3 that end portions 100 and 164 of connecting segment 12 extend perpendicular to bottom surface 186. There is no rounded transition, as with ends 188 and 190, so that bottom surface 186 acts as a stop for saddle bearings 50 and 138 to prevent hyper extensions of the ulnar and humeral bones.

Because of the difference in the tightness between the connections of the ulnar and humeral members 10 and 14, respectively, there is a preferential motion of about 10° of rotation which takes place at the ulnar member 10 because it is not as tight as the humeral member 14. The humeral member 14 will move after the ulnar member 10, thereby preventing cogwheeling instability or jerkiness. The ulnar member 10 is essentially freely rotatable about the pin 102, while the humeral member 14 requires about 3-4 in. lb. of torque for pivoting of the connecting segment 12 about the pin 174 to occur. We also prefer that the aperture 78 be slightly larger than the aperture 76, in order to further permit the side ways motion to occur. Aperture 78 may be 10 mm., while aperture 76 may be 8 mm.

Should the connecting segment 12, saddle bearings 50 and 138, or bearings 86 and 166 need to be replaced, either because of wear or the patient has grown so that the spacing of segment 12 is insufficient, then those components may be replaced while the humeral and ulnar members 14 and 10, respectively, remain fixed in their medullary canals. It is merely necessary to remove snap rings 110 and 182 in order to disassemble the components and then to replace them.

While this invention has been described as having a preferred design, it is understood that it is capable of further modifications, uses, and/or adaptations of the invention following in general the principle of the invention and including such departures from the present disclosure has come within known or customary practice in the art to which the invention pertains, and as may be applied to the essential features set forth, and falls within the scope of the invention or the limits of the appended claims.

What we claim:

1. An artificial elbow, comprising:
   a) a humeral member and an ulnar member;
   b) a connecting segment having first and second ends; and
   c) first means connecting said humeral member to said first end for pivotal rotation relative thereto only in response to a torque which is equal to or greater than a first minimum torque, and second means connecting said ulnar member to said second end for pivotal rotation relative thereto only in response to a torque which is equal to or greater than a second minimum torque, said second minimum torque being less than said first minimum torque.

2. The elbow of claim 1, wherein:
   a) said first end has thickness exceeding the thickness of said second end.

3. The elbow of claim 2, wherein:
   a) said segment is formed from a polymeric material.

4. The elbow of claim 1, wherein:
   a) said humeral member is force fit secured to said first end.

5. The elbow of claim 1, wherein:
   a) each of said ends has an opening therethrough and said openings extend in parallel; and
   b) a pin assembly extends through each of said openings and is operably secured to an associated one of said members for therewith defining a pivot axis.

6. The elbow of claim 5, wherein:

a) each of said members includes a yoke having first and second arms, each yoke surrounding the associated end.

7. The elbow of claim 6, wherein:
a) one arm of each yoke has an aperture therethrough and the other arm thereof has a detent therein, the aperture has a diameter exceeding the diameter of the detent.

8. The elbow of claim 7, wherein:
a) a clip is positioned within each of said apertures for securing the associated pin assembly therein.

9. The elbow of claim 6, wherein:
a) each of said yokes is U-shaped, and the associated arms extend in parallel and are juxtaposed to an associated side of the associated segment end.

10. The elbow of claim 9, further comprising:
a) first and second saddle bearings, each saddle bearing complementing one of said yokes and secured thereto and each saddle bearing has first and second arms juxtaposed to the associated arms of the associated yoke.

11. The elbow of claim 10, wherein:
a) each arm of each of said saddle bearings has an aperture therethrough aligned with the opening in the associated segment end, and each saddle bearing aperture has a diameter at least equal to the diameter of the associated pin assembly.

12. The elbow of claim 11, wherein:
a) said ulnar member saddle bearing arms are spaced apart a distance exceeding the thickness of said segment second end so that said ulnar member may pivot about an axis extending transverse to said second end pin assembly.

13. The elbow of claim 12, wherein:
a) said humeral member saddle bearing arms are spaced apart a distance corresponding substantially to the thickness of said segment first end so that said humeral member may pivot only about said first end pin assembly.

14. The elbow of claim 12, wherein:
a) said ulnar member saddle bearing is U-shaped, and has a base portion from opposites ends of which an arm extends;
b) said segment second end has an arcuate portion; and
c) said base portion is arcuate and is engaged with said second end arcuate portion for limiting pivoting of said ulnar member about said transverse axis.

15. The elbow of claim 12, wherein:
a) each of said saddle bearings is formed from a polymeric material.

16. The elbow of claim 15, wherein:
a) said polymeric material is ultra high molecular weight polyethylene.

17. The elbow of claim 16, wherein:
a) each of said members is formed of metal.

18. The elbow of claim 10, wherein:
a) each of said yokes has a portion thereof receiving and surrounding a cooperating portion of the associated saddle bearing.

19. The elbow of claim 18, wherein:
a) one of said portions is a tongue, and the other of said portions is a groove.

20. The elbow of claim 19, wherein:
a) said groove is formed in said yoke and extends generally transverse to the associated pin assembly; and b) said tongue is formed on said saddle bearing.

21. The elbow of claim 5, wherein:
a) each pin assembly includes a pin and a cylindrical bearing surrounding the pin, and each cylindrical bearing has a diameter substantially equal to the diameter of the associated opening.

22. The elbow of claim 21, wherein:
a) each bearing has a uniform diameter for a substantial portion of the length thereof.

23. The elbow of claim 21, wherein:
a) at least one end of each bearing is chamfered.

24. The elbow of claim 5, wherein:
a) the longitudinal axes of said pin assemblies define a plane, and said humeral member extends along said plane; and
b) said ulnar member has a substantial portion thereof spaced from and extending parallel to said plane.

25. The elbow of claim 24, wherein:
a) one of said ulnar and humeral members has a substantial portion thereof extending at an angle to the associated pin assembly.

26. The elbow of claim 1, wherein:
a) a series of ribs extends substantially the length of each of said members.

27. The elbow of claim 26, wherein:
a) said ulnar member tapers from one end thereof; and
b) said humeral member has a substantially constant cross-section the length thereof.

28. An artificial elbow, comprising:
a) a humeral member having a first yoke at a first end thereof;
b) an ulnar member having a second yoke at a first end thereof;
c) a connecting segment having integral first and second portions, said first portion having a thickness exceeding the thickness of said second portion; and
d) said first yoke frictionally secured to said first portion and pivotal relative thereto, and said second yoke loosely secured to said second portion and pivotal relative thereto.

29. The elbow of claim 28, wherein:
a) each of said portions has an aperture therethrough, and said apertures extend in parallel;
b) a pin is received in each of said apertures and extends outwardly beyond opposite sides thereof; and
c) each of said yokes is secured to one of said pins and is pivotal thereabout.

30. The elbow of claim 29, wherein:
a) a saddle bearing is received within each of said yokes, and each saddle bearing is formed of a polymeric material; and
b) each of said members is metallic.

31. The elbow of claim 29, wherein:
a) each of said yokes has first and second parallel arms, each arm extending along a side of the associated portion; and
b) one of said arms of each yoke has an aperture therethrough through which the associated pin extends, and the other arm of each of said yokes has a detent in which an end of the associated pin is received.

32. The elbow of claim 31, wherein:
a) each of said pins is metallic; and
b) a polymeric cylindrical bearing surrounds each of said pins and extends through the associated apertures.

* * * * *